United States Patent
Govari et al.

(10) Patent No.: US 10,555,776 B2
(45) Date of Patent: Feb. 11, 2020

(54) MAGNETIC RESONANCE THERMOMETRY DURING ABLATION

(71) Applicant: Biosense Webster (Israel) Ltd., Yokneam (IL)

(72) Inventors: Assaf Govari, Haifa (IL); Andres Claudio Altmann, Haifa (IL); Yaron Ephrath, Karkur (IL); Vadim Gliner, Haifa (IL); Eyal Dror, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 308 days.

(21) Appl. No.: 15/425,166

(22) Filed: Feb. 6, 2017

(65) Prior Publication Data
US 2017/0258530 A1    Sep. 14, 2017

Related U.S. Application Data

(60) Provisional application No. 62/305,026, filed on Mar. 8, 2016.

(51) Int. Cl.
*A61B 34/20* (2016.01)
*A61B 5/055* (2006.01)
(Continued)

(52) U.S. Cl.
CPC .............. *A61B 34/20* (2016.02); *A61B 5/055* (2013.01); *A61B 5/065* (2013.01);
(Continued)

(58) Field of Classification Search
CPC ......... A61B 34/20; A61B 5/055; A61B 5/065; A61B 18/1492; A61B 2034/2051; A61B 2034/2065; A61B 2090/3954; A61B 2018/00351; A61B 2018/00577; A61B 2018/00791; A61B 2090/374; A61B 18/12; A61B 18/14; A61B 2018/00595; A61B 2018/1467; G01R 33/287; G01R 33/4804;
(Continued)

(56) References Cited

U.S. PATENT DOCUMENTS 6,226,542 B1  5/2001  Reisfeld
6,301,496 B1  10/2001  Reisfeld
(Continued)

OTHER PUBLICATIONS

EP Search Report From Counterpart EP17159516.8 dated Jul. 28, 2017.
(Continued)

*Primary Examiner* — Sanjay Cattungal
(74) *Attorney, Agent, or Firm* — Notaro, Michalos & Zaccaria P.C.

(57) ABSTRACT

Thermography of an ablation site is carried out by navigating a probe into contact with target tissue in the heart, obtaining a first position of a position sensor in the probe and acquiring a first magnetic resonance thermometry image of the target tissue. The method is further carried out during ablation by iteratively reading the position sensor to obtain second positions, and acquiring a new magnetic resonance thermometry image of the target tissue when the distance between the first position and one of the second positions is less than a predetermined distance. The images are analyzed to determine the temperature of the target tissue.

21 Claims, 4 Drawing Sheets

(51) Int. Cl.
    *A61B 5/06* (2006.01)
    *A61B 18/14* (2006.01)
    *G01R 33/28* (2006.01)
    *G01R 33/48* (2006.01)
    *A61B 90/00* (2016.01)
    *G01R 33/563* (2006.01)
    *G01R 33/56* (2006.01)
    *G01R 33/50* (2006.01)
    *A61B 18/00* (2006.01)

(52) U.S. Cl.
    CPC ........ *A61B 18/1492* (2013.01); *G01R 33/287* (2013.01); *G01R 33/4804* (2013.01); *A61B 2018/00351* (2013.01); *A61B 2018/00577* (2013.01); *A61B 2018/00791* (2013.01); *A61B 2034/2051* (2016.02); *A61B 2034/2065* (2016.02); *A61B 2090/374* (2016.02); *A61B 2090/3954* (2016.02); *G01R 33/50* (2013.01); *G01R 33/5605* (2013.01); *G01R 33/56341* (2013.01)

(58) Field of Classification Search
    CPC ................ G01R 33/50; G01R 33/5605; G01R 33/56341
    USPC .................................................. 600/407–430
    See application file for complete search history.

(56) References Cited

U.S. PATENT DOCUMENTS

| | | | |
|---|---|---|---|
| 6,575,969 B1 * | 6/2003 | Rittman, III | A61B 18/1482 606/41 |
| 6,814,733 B2 | 11/2004 | Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 7,756,576 B2 | 7/2010 | Levin | |
| 8,052,604 B2 * | 11/2011 | Lau | A61B 8/12 600/439 |
| 8,825,133 B2 | 9/2014 | Jenkins et al. | |
| 2007/0216410 A1 * | 9/2007 | Thelissen | G01R 33/4804 324/315 |
| 2011/0046472 A1 * | 2/2011 | Schmidt | G01R 33/4804 600/411 |
| 2011/0175615 A1 | 7/2011 | Grissom et al. | |
| 2012/0157890 A1 * | 6/2012 | Govari | A61B 18/20 601/3 |
| 2012/0209260 A1 | 8/2012 | Lambert et al. | |
| 2012/0296197 A1 | 11/2012 | Vahala et al. | |
| 2013/0023862 A1 * | 1/2013 | Marrouche | A61N 7/02 606/3 |
| 2013/0102880 A1 | 4/2013 | Gulsen et al. | |
| 2015/0099965 A1 | 4/2015 | Volland et al. | |
| 2016/0008024 A1 * | 1/2016 | Payne | A61N 7/02 606/169 |

OTHER PUBLICATIONS

Jing Yuan et al. Towards Fast and Accurate Temperature Mapping With Proton Resonance Frequency-Based MR Thermometry. Quant Imaging Med Surg. Mar. 2012;2(1):21-32.
Hey S. et al. Towards Optimized MR Thermometry of the Human Heart at 3T. NMR Biomed Jan. 2012;25(1):35-43.
Volland N.A. et al. Initial Feasibility Testing of Limited Field of View Magnetic Resonance Thermometry Using a Local Cardiac Radiofrequency Coil. Magn Reson Med Oct. 2013;70(4):994-1004.
U.S. Appl. No. 62/305,026, filed Mar. 8, 2016.

* cited by examiner

MAGNETIC RESONANCE THERMOMETRY DURING ABLATION

CROSS-REFERENCE TO RELATED APPLICATIONS

This Application claims the benefit of U.S. Provisional Application No. 62/305,026, which is herein incorporated by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to devices and methods for transferring non-mechanical forms of energy to or from the body. More particularly, this invention relates to magnetic resonance thermometry during cardiac ablation therapy.

2. Description of the Related Art

The meanings of certain acronyms and abbreviations used herein are given in Table 1.

TABLE 1

| Acronyms and Abbreviations | |
|---|---|
| GRE | Gradient-Recalled Echo |
| MRI | Magnetic Resonance Imaging |
| PRF | Proton Resonance Frequency |
| TE | Echo Time |

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in myocardial tissue associated with cardiac ganglionic plexi. In this condition, after unwanted signals are generated in the pulmonary veins or conducted through the pulmonary veins from other sources, they are conducted into the left atrium where they can initiate or continue arrhythmia.

Procedures for treating arrhythmia include disrupting the areas causing the arrhythmia by ablation, as well as disrupting the conducting pathway for such signals. Ablation of body tissue using electrical energy is known in the art. The ablation is typically performed by applying alternating currents, for example radiofrequency energy, to one or more ablation electrodes, at a sufficient power to destroy target tissue. Typically, the electrodes are mounted on the distal tip or portion of an invasive probe or catheter, which is inserted into a subject. The distal tip may be tracked in a number of different ways known in the art, for example by measuring magnetic fields generated at the distal tip by coils external to the subject.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

Various techniques have been developed to control local heating of the ablation site. For example commonly assigned U.S. Pat. No. 6,997,924 to Govari et al., which is herein incorporated by reference, describes a technique of limiting heat generated during ablation by determining a measured temperature of the tissue and a measured power level of the transmitted energy, and controlling the power output level responsively to a function of the measured temperature and the measured power level. This patent, like other examples, relies on measurements of the temperature at the ablation site. Typically, a temperature sensor such as a thermocouple or thermistor, may be mounted on or near the ablation electrodes.

Magnetic resonance thermometry based on the proton resonance frequency (PRF), has been proposed for intrabody temperature measurements. A phase shift in the PRF is linear over a wide temperature range, and is relatively insensitive to tissue type. PRF-based phase imaging has become a favored technique for MRI thermometry.

The principles of PRF-based phase imaging are well-known. Briefly, the nuclear shielding effect of electrons in an aqueous medium increases with temperature, leading to reduced local magnetic field strength and hence a reduced PRF. This can be exploited by choosing a gradient-recalled echo (GRE) imaging pulse sequence for acquiring multiple phase images during heating such that the phase differences of the dynamic images are proportional to the echo time (TE). Under these conditions, the temperature change $\Delta T(t)$ may be calculated:

$$\Delta T(t) = \frac{\Delta \Phi(t)}{\gamma \cdot \alpha \cdot B_0 \cdot TE} = \frac{\Phi(t) - \Phi_0}{\gamma \cdot \alpha \cdot B_0 \cdot TE}, \quad (1)$$

where $\Phi(t)$ and $\Phi_0$ are the image phase at time t and an initial time, respectively; $\gamma$ is the gyromagnetic ratio of hydrogen (42.58 MHz per Tesla); $\alpha$ is the temperature coefficient of the shielding constant for the shielding effect; and $B_0$ is the main magnetic field strength.

However, for moving tissues, such as a beating heart, MRI images in sequence are generally not in registration with one another. Accurate thermometry is not possible, because any observed phase change could be due, at least in part, to a movement in the target being imaged.

SUMMARY OF THE INVENTION

Disclosed embodiments of the invention involve locating a catheter at the tissue ablation site. The catheter has a position sensor at its distal tip, and an electrode on the distal tip is used for ablation, the ablation causing a change of temperature desired to be tracked. The position information obtained from the sensor readings provides an indication that the relevant part of the field of view of the imaging system is in registration with that of a previous image. The indication triggers acquisition of a new image.

There is provided according to embodiments of the invention a method, which is carried out by inserting a probe into a heart of a living subject. The probe has a position sensor and an ablation electrode disposed on its distal portion. The method is further carried out by navigating the probe into a contacting relationship with target tissue of the heart, activating the ablation electrode, obtaining a first reading of the position sensor to obtain a first position, and acquiring a first magnetic resonance thermometry image of the target tissue at the first position. The method is further carried out iteratively by taking new readings of the position sensor to obtain second positions, acquiring a new magnetic resonance thermometry image of the target tissue when a distance between the first position and one of the second positions is less than a predetermined distance, and analyzing the first magnetic resonance thermometry image and the new magnetic resonance thermometry image to determine the temperature of the target tissue.

According to one aspect of the method, acquiring the first magnetic resonance thermometry image and the new magnetic resonance thermometry image includes determining a phase change therebetween of a proton resonant frequency and calculating the temperature of the target tissue from the phase change.

According to a further aspect of the method, the position sensor is a magnetic location sensor and the new readings are taken at 10 ms intervals.

According to still another aspect of the method, acquiring the first magnetic resonance thermometry image and the new magnetic resonance thermometry image comprise measuring a proton resonance frequency phase shift and correlating the phase shift with temperature.

According to an additional aspect of the method, the first magnetic resonance thermometry image and the new magnetic resonance thermometry image are obtained from pulse sequences.

According to another aspect of the method, the pulse sequences are gradient-recalled echo pulse sequences.

According to one aspect of the method, measuring a proton resonance frequency phase shift is performed spectroscopically.

According to a further aspect of the method, acquiring the first magnetic resonance thermometry image and the new magnetic resonance thermometry image comprise measuring a proton density spin lattice relaxation time.

According to an additional aspect of the method, acquiring the first magnetic resonance thermometry image and the new magnetic resonance thermometry image comprise measuring a spin-spin relaxation time.

According to yet another aspect of the method, acquiring the first magnetic resonance thermometry image and the new magnetic resonance thermometry image comprise measuring a diffusion coefficient.

According to still another aspect of the method, acquiring the first magnetic resonance thermometry image and the new magnetic resonance thermometry image comprise measuring a magnetization transfer.

There is further provided according to embodiments of the invention an apparatus including a flexible probe adapted for insertion into a heart of a patient and having a position sensor in its distal portion. A processor is linked to the position sensor and is configured for sending control signals to a magnetic resonance imager. The processor is cooperative with the magnetic resonance imager for obtaining a first reading of the position sensor to establish a first position when the distal portion is in a contacting relationship with target tissue of the heart, acquiring a first magnetic resonance thermometry image of the heart at the first position, and during ablation thereafter iteratively taking new readings of the position sensor to obtain second positions, acquiring a new magnetic resonance thermometry image of the target tissue when a distance between the first position and one of the second positions is less than a predetermined distance, and analyzing the first magnetic resonance thermometry image and the new magnetic resonance thermometry image to determine a temperature of the target tissue.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview

Figure 1:
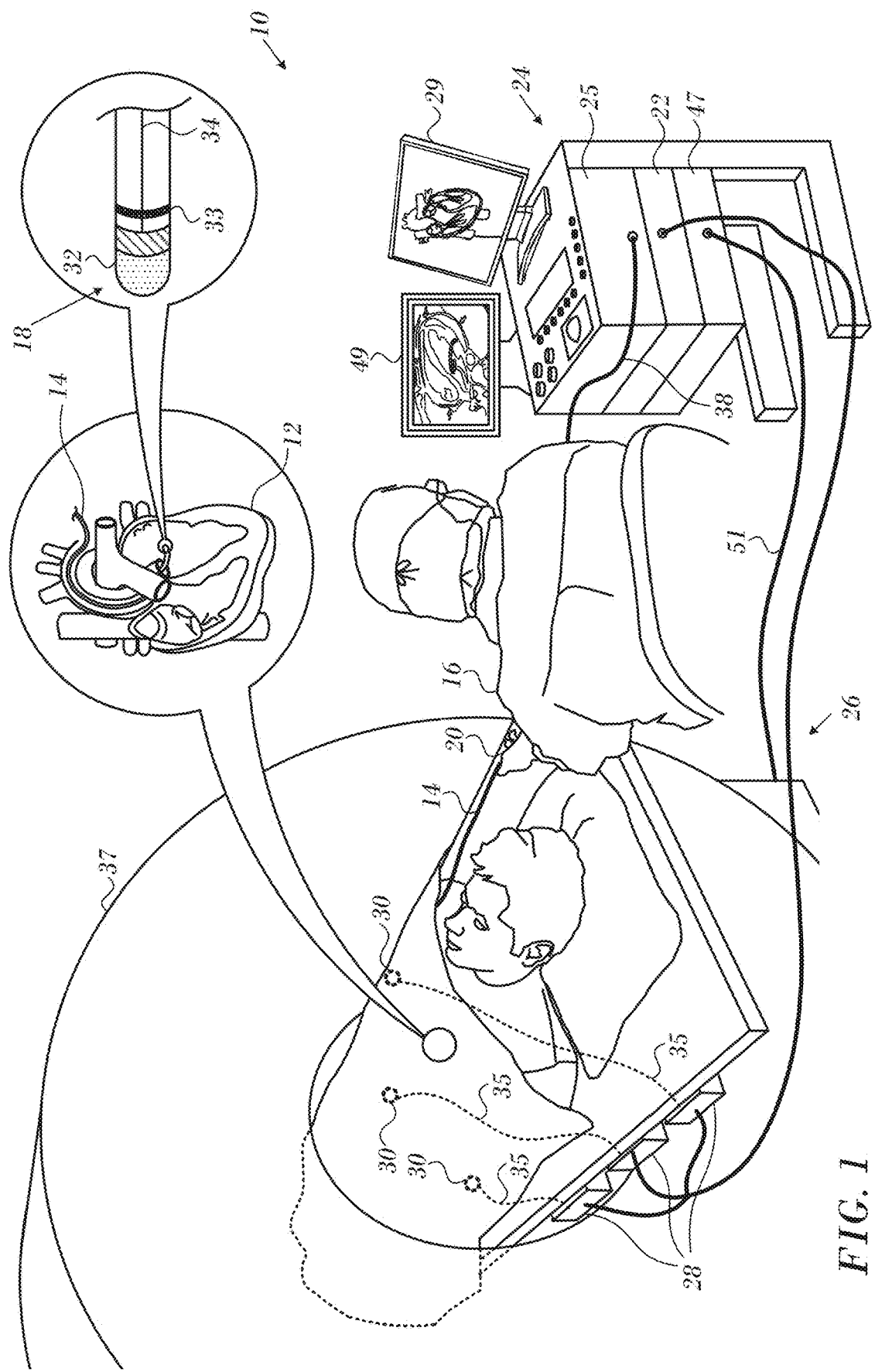
FIG. 1 is a pictorial illustration of a system for performing cardiac catheterization procedures in accordance with an embodiment of the invention.

Turning now to the drawings, reference is initially made to FIG. 1, which is a pictorial illustration of a system 10 for performing cardiac catheterization procedures on a heart 12 of a living subject, which is constructed and operative in accordance with a disclosed embodiment of the invention. The system 10 typically comprises a general purpose or embedded computer processor, which is programmed with suitable software for carrying out the functions described hereinbelow. Thus, although portions of the system 10 shown in FIG. 1 and other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. Alternatively or additionally, the system 10 may comprise a digital signal processor or hard-wired logic.

The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 22 located in a console 24, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765, which is capable of producing electroanatomic maps of the heart as required for the ablation. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating (or cooling) it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and/or one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference.

The console 24 typically contains one or more ablation power connections. The catheter 14 may be adapted to conduct ablative energy to the heart using any known ablation technique, e.g., radiofrequency energy, ultrasound energy, freezing technique and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

A MRI imaging device 37 is linked to a control processor 47, which may be located in the console 24. An operator may select or override automatic operation to control the operation of the MRI imaging device 37, for example by revising imaging parameters. The control processor 47 may communicate with the MRI imaging device 37 via a cable 51 to enable and disable the MRI imaging device 37 to acquire image data. An optional display monitor 49, linked to the control processor 47, allows the operator to view images produced by the MRI imaging device 37. When the display monitor 49 is not included, the images may still be viewed on a monitor 29, either via a split screen or in alternation with other images.

As noted above, the catheter 14 is coupled to the console 24, which enables the operator 16 to observe and regulate the functions of the catheter 14. The processor 22 is typically a computer with appropriate signal processing circuits. The processor 22 is coupled to drive the monitor 29. The signal processing circuits typically receive, amplify, filter and digitize signals from the catheter 14 and the MRI imaging device 37, including signals generated by the above-noted sensors and a plurality of location sensing electrodes (not shown) located distally in the catheter 14. The digitized signals are received and used by the console 24 and the positioning system to compute the position and orientation of the catheter 14, analyze the electrical signals from the electrodes and generate desired electroanatomic maps. The above-described arrangement works well when a coordinate system is shared between system components, e.g., a combined CARTO-MRI system. This is especially useful when ablating the atria, as its wall is very thin, and it is necessary to define its boundaries. Despite advances in image processing, edge detection of the endocardial wall continues to be challenging, and conventionally requires manual analysis of sequential slice images. However, with a trackable, MRI-compatible, indwelling catheter that touches the endocardial wall and measures contact-force, manual analysis can be avoided.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally placed catheter, which is inserted into the heart 12 maintained in a fixed position relative to the heart 12. Conventional pumps and lines for circulating liquids through the catheter 14 for cooling the ablation site are provided.

Image Acquisition

Figure 2:
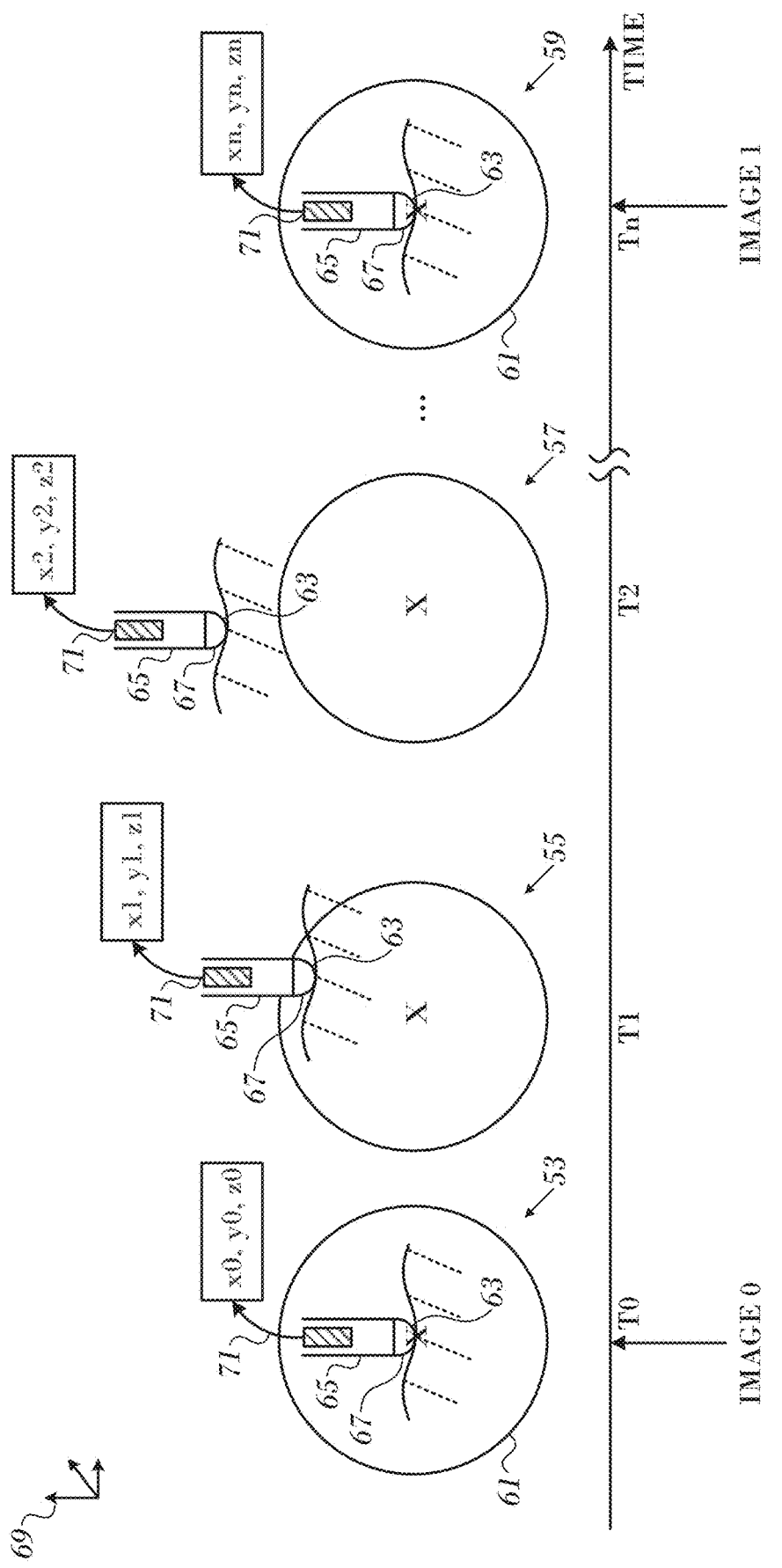
FIG. 2 is a series of diagrams illustrating the acquisition of MRI thermometry images from a moving tissue in accordance with an embodiment of the invention.

Reference is now made to FIG. 2, which is a series of diagrams 53, 55, 57, 59 illustrating the acquisition of MRI thermometry images from a moving tissue in accordance with an embodiment of the invention. An area being imaged by MRI imaging device 37 (FIG. 1) is indicated by a circle 61. In diagram 53 a point of interest, shown here as an ablation site 63 of a heart is marked by "X" at the center of the circle 61. The distal end of a probe 65 has an ablation electrode 67 in contact with the ablation site 63. The position of the circle 61 is constant.

From the readings, the location of the ablation site 63 with respect to a frame of reference 69 can be determined from readings of a position sensor 71, which is typically a magnetic location sensor. The ablation site 63 is aligned with the "X" of circle 61 at time $T_0$ and has coordinates $(x_0, y_0, z_0)$. An MRI thermometry image ($IMAGE_0$) is acquired at time $T_0$. However, at times $T_1, T_2$, cardiorespiratory motions have displaced the ablation site 63 and probe 65 with respect to the circle 61 as shown in diagrams 55, 59. At times $T_1, T_2$ the ablation site 63 has coordinates $(x_1, y_1, z_1)$, $(x_2, y_2, z_2)$ respectively, which differ from the coordinates $(x_0, y_0, z_0)$. At time $T_n$. The ablation site 63 has coordinates $(x_n, y_n, z_n)$, which are recognized by the system as being essentially identical to the coordinates $(x_0, y_0, z_0)$, i.e., a distance measure between two sets of coordinates that is less than a pre-defined limit δ. For example, the Euclidian distance $$\sqrt{(x_n-x_r)^2+(y_n-y_r)^2+(z_n-z_r)^2}<\delta, \quad (2)$$

where $(x_r, y_r, z_r)$ are coordinates of a reference point corresponding to the ablation site on a reference image.

The recognition triggers acquisition of a second MRI thermometry image ($IMAGE_1$). Currently available sensors are capable of reporting a position every 10 ms. Suitable parameters for the MRI image are TE 40 ms, slice thickness 3 mm and flip angle 60 degrees. The MRI thermometry images may be triggered at every beat to acquire a new slice during the time interval $T_0<T<T_n$.

Figure 3:
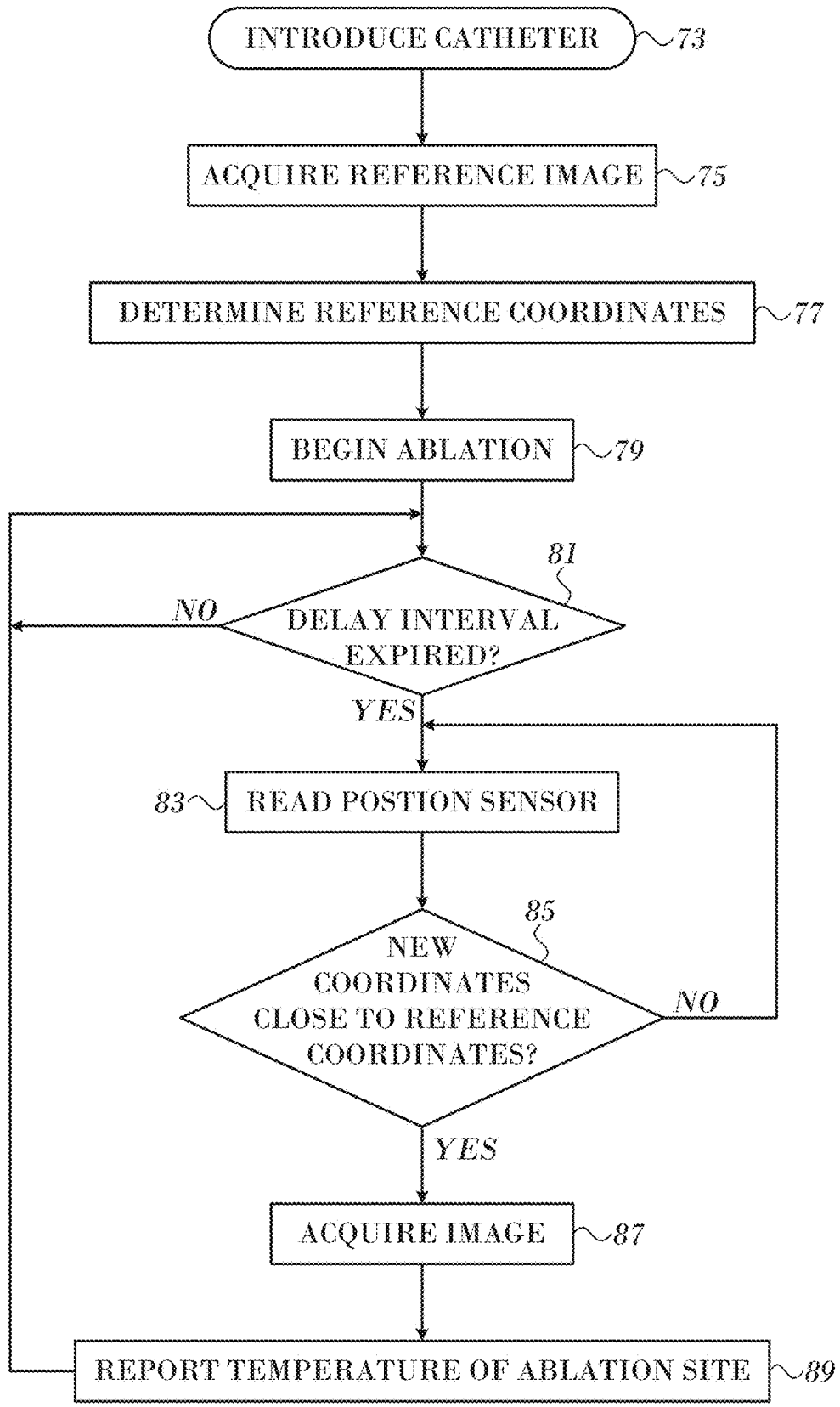
FIG. 3 is a flow chart of a method of determining the temperature of an ablation site, in accordance with an embodiment of the invention.

Reference is now made to FIG. 3, which is a flow chart of a method of determining the temperature of an ablation site, in accordance with an embodiment of the invention. The procedure is described with respect to the exemplary system 10 (FIG. 1), but may be performed with other system configurations. The process steps are shown in a particular linear sequence in FIG. 3 for clarity of presentation. However, it will be evident that many of them can be performed in parallel, asynchronously, or in different orders. Those skilled in the art will also appreciate that a process could alternatively be represented as a number of inter-related states or events, e.g., in a state diagram. Moreover, not all illustrated process steps may be required to implement the method.

At initial step 73 the heart is catheterized conventionally with a probe having a position sensor and an ablation electrode in its distal portion. The ablation electrode is brought into contact with a target location using known methods.

Next, at step 75 a reference image including the target area is acquired on the MRI imaging device 37. Ambient body temperature is assumed for purposes of correlating the PRF phase in the reference image with temperature.

Next, at step 77 the position sensor 71 is read and reference coordinates $(x_r, y_r, z_r)$ of the sensor and the target location are determined on the reference image.

Next, at step 79 the ablation electrode is activated to begin ablation of the target tissue.

MRI thermometry images such as PRF-based phase images are acquired during the procedure from time to time. One suitable pulse sequence for the images is a gradient-recalled echo pulse sequence with the above-noted MRI parameters. A pause occurs at delay step 81 where it is determined if a predetermined delay interval has expired. If the MRI thermometry images are to be acquired continually, then the delay interval is set to zero.

Next, at step 83 a reading is obtained from the position sensor 71 and its coordinates $(x_n, y_n, z_n)$ determined.

Next, at decision step 85, it is determined if the distance between the coordinates obtained at step 77 and step 83 is smaller than a predetermined value δ, i.e., the inequality (2) shown above is satisfied. If the determination at decision step 85 is negative, then control returns to step 83 and another reading is obtained from the position sensor 71.

If the determination at decision step 85 is affirmative, then control proceeds to step 87. A new MRI thermometry image is acquired.

Then, at step 89 the temperature at the ablation site is determined on the new image, typically by PRF-based phase temperature mapping, and deriving the temperature of the ablation site from the frequency phase shift, using the principles of equation (1) given above. Control then returns to delay step 81 to begin a new waiting period.

Alternate Embodiments

The PRF shift with temperature can be measured spectroscopically, using a reference substance such as a lipid, which is temperature independent. Alternatively, there are a number of temperature-dependent characteristics in magnetic resonance imaging, for example, proton density spin lattice relaxation time; spin-spin relaxation time; diffusion coefficient and magnetization transfer. Shifts in the measurements of these characteristics may be determined in the analysis of the MRI images in step 89 (FIG. 3).

Example

Figure 4:
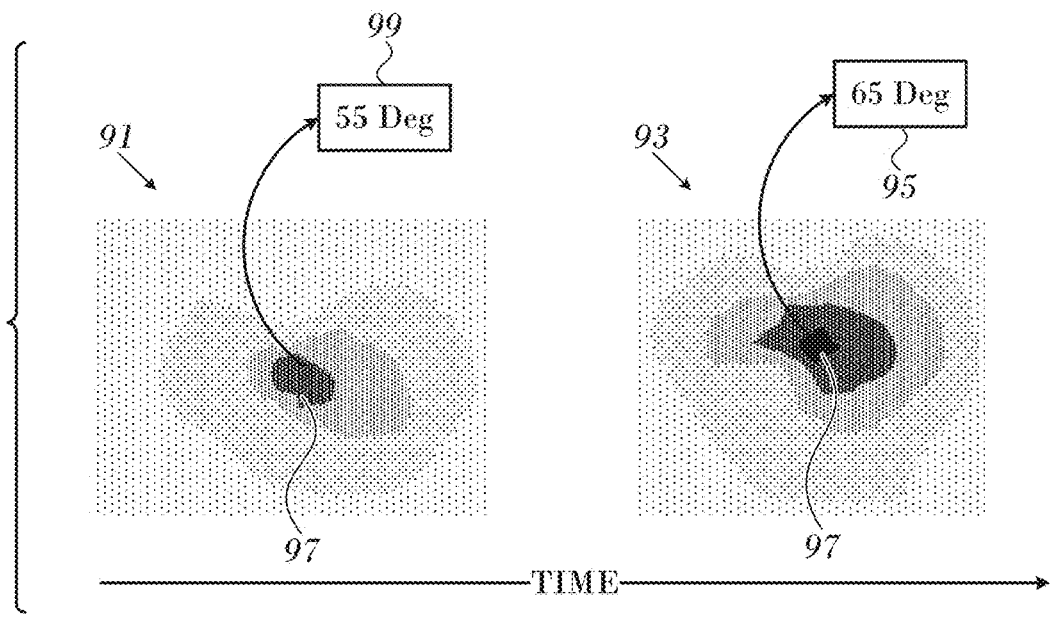
FIG. 4 is a composite diagram comprising two MRI thermography images acquired in accordance with an embodiment of the invention.

Reference is now made to FIG. 4, which is a composite diagram comprising two MRI thermography images 91, 93 showing typical results in a prospective cardiac ablation procedure in accordance with an embodiment of the invention. An increase in temperature 95 at ablation site 97 is noted in the later image 93, compared to temperature 99 in the earlier image 91. The operator can react to the measured temperatures 95, 99 by adjusting the power and/or duration of the ablation procedure as is known in the art.

Figure 5:
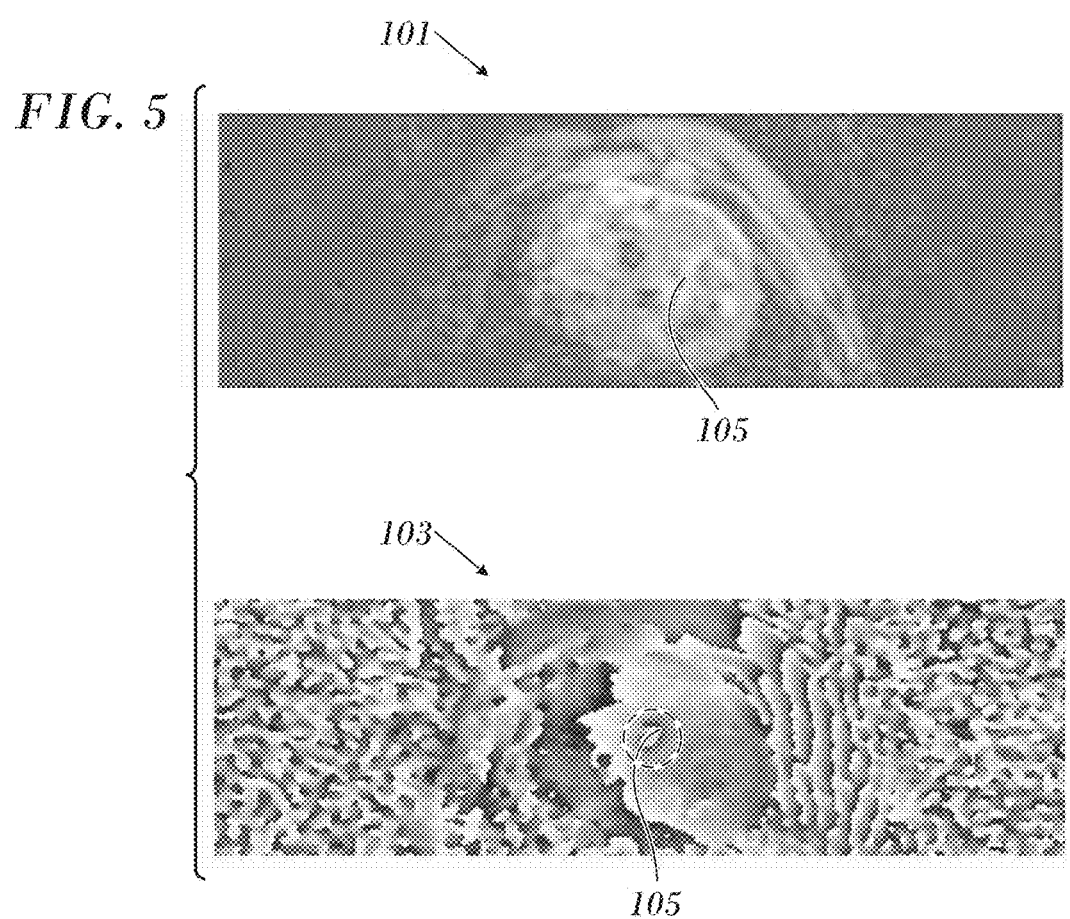
FIG. 5 is a collection of two MRI images that are suitable for MRI thermography.

Reference is now made to FIG. 5, which is a collection of two MRI images 101, 103 that are suitable for MRI thermography according to an embodiment of the invention. The images 101, 103 were obtained from data acquired in one slice in accordance with an embodiment of the invention. Images 101, 103 are an amplitude and a phase image, respectively. Ablation site 105 is indicated on both images.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   inserting a probe into a heart of a living subject, the probe having a distal portion, a position sensor and an ablation electrode being disposed on the distal portion;
   navigating the probe into a contacting relationship with a target tissue of the heart and activating the ablation electrode;

obtaining a first reading of the position sensor to obtain a first position of the probe in the heart;

acquiring a first magnetic resonance thermometry image of the target tissue at the first position; and thereafter during ablation iteratively performing the steps of:

taking new readings of the position sensor to obtain second positions of the probe in the heart;

acquiring a new magnetic resonance thermometry image of the target tissue only when a distance between the first position and one of the second positions is less than a predetermined distance; and analyzing the first magnetic resonance thermometry image and the new magnetic resonance thermometry image to determine a temperature of the target tissue.

2. The method according to claim 1, wherein acquiring the first magnetic resonance thermometry image and the new magnetic resonance thermometry image comprises determining a phase change therebetween of a proton resonant frequency and calculating the temperature of the target tissue from the phase change.

3. The method according to claim 1, wherein the position sensor is a magnetic location sensor and the new readings are taken at 10 ms intervals.

4. The method according to claim 1, wherein acquiring the first magnetic resonance thermometry image and the new magnetic resonance thermometry image comprise measuring a proton resonance frequency phase shift and correlating the phase shift with temperature.

5. The method according to claim 4, wherein the first magnetic resonance thermometry image and the new magnetic resonance thermometry image are obtained from pulse sequences.

6. The method according to claim 5, wherein the pulse sequences are gradient-recalled echo pulse sequences.

7. The method according to claim 4, wherein measuring a proton resonance frequency phase shift is performed spectroscopically.

8. The method according to claim 1, wherein acquiring the first magnetic resonance thermometry image and the new magnetic resonance thermometry image comprise measuring a proton density spin lattice relaxation time.

9. The method according to claim 1, wherein acquiring the first magnetic resonance thermometry image and the new magnetic resonance thermometry image comprise measuring a spin-spin relaxation time.

10. The method according to claim 1, wherein acquiring the first magnetic resonance thermometry image and the new magnetic resonance thermometry image comprise measuring a diffusion coefficient.

11. The method according to claim 1, wherein acquiring the first magnetic resonance thermometry image and the new magnetic resonance thermometry image comprise measuring a magnetization transfer.

12. The method according to claim 1, wherein when the distance between the first position and one of the second positions is greater than the predetermined distance then acquiring a new magnetic resonance thermometry image of the target tissue.

13. An apparatus comprising:

a flexible probe having a proximal portion and a distal portion adapted for insertion into a heart of a patient;

a position sensor and an ablation electrode in the distal portion;

a processor linked to the position sensor and configured for sending control signals to a magnetic resonance imager, the processor cooperative with the magnetic resonance imager for:

obtaining a first reading of the position sensor to obtain a first position during ablation of a target tissue of the heart;

acquiring a first magnetic resonance thermometry image of the heart at the first position; and thereafter during ablation with the ablation electrode iteratively performing the steps of:

taking new readings of the position sensor to obtain second positions of the probe in the heart;

acquiring a new magnetic resonance thermometry image of the target tissue only when a distance between the first position and one of the second positions is less than a predetermined distance; and analyzing the first magnetic resonance thermometry image and the new magnetic resonance thermometry image to determine a temperature of the target tissue.

14. The apparatus according to claim 13, wherein the first magnetic resonance thermometry image and the new magnetic resonance thermometry image are proton resonance frequency phase images.

15. The apparatus according to claim 13, wherein the first magnetic resonance thermometry image and the new magnetic resonance thermometry image are obtained from pulse sequences.

16. The apparatus according to claim 15, wherein the pulse sequences are gradient-recalled echo pulse sequences.

17. The apparatus according to claim 13, wherein acquiring the first magnetic resonance thermometry image and the new magnetic resonance thermometry image comprise measuring a proton density spin lattice relaxation time.

18. The apparatus according to claim 13, wherein acquiring the first magnetic resonance thermometry image and the new magnetic resonance thermometry image comprise measuring a spin-spin relaxation time.

19. The apparatus according to claim 13, wherein acquiring the first magnetic resonance thermometry image and the new magnetic resonance thermometry image comprise measuring a diffusion coefficient.

20. The apparatus according to claim 13, wherein acquiring the first magnetic resonance thermometry image and the new magnetic resonance thermometry image comprise measuring a magnetization transfer.

21. The apparatus according to claim 13, wherein when the distance between the first position and one of the second positions is greater than the predetermined distance then acquiring a new magnetic resonance thermometry image of the target tissue.

* * * * *